United States Patent [19]

West

[11] Patent Number: 4,906,660

[45] Date of Patent: Mar. 6, 1990

[54] WOOD PRESERVATIVE COMPOSITION AND METHOD

[75] Inventor: Michael H. West, Senatobia, Miss.

[73] Assignee: Chapman Chemical Company, Memphis, Tenn.

[21] Appl. No.: 49,101

[22] Filed: May 13, 1987

[51] Int. Cl.$^4$ .............................................. A61K 31/30
[52] U.S. Cl. ................................................... 514/499
[58] Field of Search ....................... 514/499, 500, 492; 424/140, 638

[56] References Cited

FOREIGN PATENT DOCUMENTS 0039538  11/1981  European Pat. Off. ............ 514/499

Primary Examiner—Douglas W. Robinson
Assistant Examiner—R. Kearse
Attorney, Agent, or Firm—Fred Philpitt

[57] ABSTRACT

A wood preservative composition and method comprising an aqueous solution of a monoalkanolamine and a copper octoate.

8 Claims, No Drawings

WOOD PRESERVATIVE COMPOSITION AND METHOD

Copper octoate compositions, such as the copper 2-ethyl hexoate and copper caprylate varieties, are known to be effective wood preservatives. These are oil-soluble compounds which are typically diluted with mineral spirits, diesel fuel, or heavy oil to yield 1% or sometimes 2%, copper metal solutions for application to wood. The increasing cost and scarcity of petroleum, coupled with its toxicity and other drawbacks makes oil-carried preservatives less than desirable.

I have found that lower straight and substituted monoalkanolamines mixed with water are effective for producing water-soluble copper octoate compositions which are suitable for application to wood. Unlike ammonia these alkanolamines are relatively odorless and exhibit low skin irritation. Compared with ammonia they have low volatility. They stay in water solution long enough to allow for practical use in open containers. When applied to wood, alkanolamine-copper octoate compositions are rendered acidic and water-insoluble in the wood. These compositions provide preservation equal to, or greater than, that provided by mineral spirits solutions of copper octoate.

The preferred alkanolamines of my invention are monoethanolamine and monoisopropanolamine. They are used in amounts ranging from about 0.6 parts to about 1.5 parts by weight for each part by weight of copper octoate. The compositions of my invention may be produced as 1% or 2% copper metal solutions in water or they may be produced as liquid concentrates suitable for dilution with water to the preferred 1% or 2% copper metal concentrations for application to wood. Decreasing the amount of copper below 1% usually reduces effectiveness and increasing the amount of copper above 2% does not result in enough added effectiveness to justify the cost.

EXAMPLE 1 (CONCENTRATES)

Copper caprylate was prepared by reacting stoichiometric quantities of copper carbonate and caprylic acid. This copper caprylate was added to water-alkanolamine mixtures, warmed to 120° F. and mixed for one hour to produce water-soluble wood preservative concentrate compositions suitable for further water dilution and then application to wood. Individual concentrate formulations were as follows:

| | Components | Weight Fraction |
|---|---|---|
| (a) | copper caprylate | 0.3495 |
| | water | 0.3505 |
| | monoethanolamine | 0.3000 |
| (b) | copper caprylate | 0.3495 |
| | water | 0.4505 |
| | monoethanolamine | 0.2000 |
| (c) | copper caprylate | 0.3495 |
| | water | 0.2505 |
| | monoethanolamine | 0.4000 |
| (d) | copper caprylate | 0.3495 |
| | water | 0.3505 |
| | monoisopropanolamine | 0.3000 |
| (e) | copper caprylate | 0.3495 |
| | water | 0.4505 |
| | monoisopropanolamine | 0.2000 |
| (f) | copper caprylate | 0.3495 |
| | water | 0.2505 |
| | monoisopropanolamine | 0.4000 |

EXAMPLE II (COMPOSITIONS)

A commercial copper 2-ethyl hexoate containing 12% copper was added to water-alkanolamine mixtures and agitated for twenty minutes to produce water-soluble wood preservative compositions suitable for application to various types of wood. Individual formulations were as follows:

| | Components | Weight Fraction |
|---|---|---|
| (a) | copper 2-ethyl hexoate (12% copper) | 0.1667 |
| | monoethanolamine | 0.0800 |
| | water | 0.7533 |
| (b) | copper 2-ethyl hexoate (12% copper) | 0.1667 |
| | monoethanolamine | 0.1200 |
| | water | 0.7133 |
| (c) | copper 2-ethyl hexoate (12% copper) | 0.1667 |
| | monoethanolamine | 0.1600 |
| | water | 0.6733 |
| (d) | copper 2-ethyl hexoate (12% copper) | 0.1667 |
| | monoisopropanolamine | 0.0800 |
| | water | 0.7533 |
| (e) | copper 2-ethyl hexoate (12% copper) | 0.1667 |
| | monoisopropanolamine | 0.1200 |
| | water | 0.7133 |
| (f) | copper 2-ethyl hexoate (12% copper) | 0.1667 |
| | monoisopropanolamine | 0.1600 |
| | water | 0.6733 |

The compositions were found to be effective as wood preservatives when subjected to standard wood preservative tests.

I claim:

1. A wood preservative composition comprising an aqueous solution of a monoalkanolamine and a copper octoate, wherein said monoalkanolamine is present in amounts ranging from about 0.6 parts to about 1.5 parts by weight for each part by weight of said copper octoate.

2. A composition according to claim 1 wherein the copper octoate is copper caprylate.

3. A composition according to claim 1 wherein the copper octoate is copper 2-ethyl hexoate.

4. A composition according to claim 1 wherein the monoalkanolamine is selected from the group consisting of monoethanolamine and monoisopropanolamine.

5. A method for preserving wood which comprises treating wood with a preservative amount of an aqueous solution of a monoalkanolamine and a copper octoate.

6. A method according to claim 5 wherein the copper octoate is copper caprylate.

7. A method according to claim 5 wherein the copper octoate is copper 2-ethyl hexoate.

8. A method according to claim 5 wherein the monoalkanolamine is monoethanolamine.

* * * * *